United States Patent
Koo et al.

(10) Patent No.: US 8,706,188 B2
(45) Date of Patent: Apr. 22, 2014

(54) AUTOMATIC SEGMENTATION OF ARTICULAR CARTILAGE FROM MRI

(75) Inventors: Seungbum Koo, Palo Alto, CA (US);
Brian A. Hargreaves, Menlo Park, CA (US); Garry E. Gold, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 1215 days.

(21) Appl. No.: 12/133,293

(22) Filed: Jun. 4, 2008

(65) Prior Publication Data

US 2009/0306496 A1    Dec. 10, 2009

(51) Int. Cl.
*A61B 5/055* (2006.01)
*G06K 9/00* (2006.01)
*G06K 9/62* (2006.01)

(52) U.S. Cl.
USPC .............................. 600/410; 382/128; 382/159

(58) Field of Classification Search
None
See application file for complete search history.

(56) References Cited

U.S. PATENT DOCUMENTS

| | | | |
|---|---|---|---|
| 5,313,532 A | 5/1994 | Harvey et al. | |
| 6,178,261 B1 | 1/2001 | Williams et al. | |
| 6,332,034 B1 | 12/2001 | Makram-Ebeid et al. | |
| 6,947,590 B2 | 9/2005 | Magarey et al. | |
| 7,239,908 B1 | 7/2007 | Alexander et al. | |
| 7,298,881 B2 * | 11/2007 | Giger et al. | 382/128 |
| 7,555,153 B2 * | 6/2009 | Martel-Pelletier et al. | 382/131 |
| 7,738,683 B2 * | 6/2010 | Cahill et al. | 382/128 |
| 8,019,801 B1 * | 9/2011 | Robb et al. | 707/899 |
| 8,204,315 B2 * | 6/2012 | Madabhushi et al. | 382/224 |
| 8,280,140 B2 * | 10/2012 | Levenson et al. | 382/133 |
| 2006/0004278 A1 * | 1/2006 | Giger et al. | 600/408 |
| 2008/0205724 A1 * | 8/2008 | Cocosco et al. | 382/130 |
| 2010/0172555 A1 * | 7/2010 | Hasezawa et al. | 382/128 |
| 2010/0260396 A1 * | 10/2010 | Brandt et al. | 382/131 |

OTHER PUBLICATIONS

Vannier et al., "Technical Developments and Instrumentation: Multispectral Analysis of Magnetic Resonance Images", Radiology, vol. 154, No. 1, pp. 221-224, Jan. 1985.
Bezdek et al., "Review of MR image segmentation techniques using pattern recognition", Med Phys. 20(4):1033-1048, 1993.
Clarke LP et al., "MRI segmentation: Methods and applications", Magnetic Resonance Imaging, vol. 13, No. 3, pp. 343-368, 1995.
Folkesson J. et al., "Segmenting articular cartilage automatically using a voxel classification approach", IEEE Trans Med Imaging, 26(1):106-15, 2007.
Koo et al., "Automatic Segmentation of Articular Cartilage from MRI: A Multi-Contrast and Multi-Dimensional Approach" Poster, 16th Annual Meeting of the International Society for Magnetic Resonance in Medicine, Toronto, Canada, May, 2008.
Koo et al., "Automatic Segmentation of Articular Cartilage from MRI: A Multi-Contrast and Multi-Dimensional Approach" Abstract accepted to International Society for Magnetic Resonance in Medicine, Jun. 27, 2007.

* cited by examiner

*Primary Examiner* — Long V. Le
*Assistant Examiner* — Angela M Hoffa
(74) *Attorney, Agent, or Firm* — Beyer Law Group LLP

(57) ABSTRACT

A method for musculoskeletal tissue segmentation used in magnetic resonance imaging (MRI) is provided. MRI image data is collected using at least two different contrast mechanisms. Voxel values from data from each contrast mechanism are used as elements of a feature vector. The feature vector is compared with classification boundaries to classify musculoskeletal tissue type of the voxel. The previous two steps are repeated for a plurality of voxels. An image is generated from the classified musculoskeletal tissue types for the plurality of voxels to provide a musculoskeletal segmentation image.

17 Claims, 6 Drawing Sheets

AUTOMATIC SEGMENTATION OF ARTICULAR CARTILAGE FROM MRI

GOVERNMENT RIGHTS

This invention was made with Government support under contract 1R01EB005790 awarded by the National Institutes of Health and contract 1R01EB002524 awarded by the National Institutes of Health. The Government has certain rights in this invention.

BACKGROUND OF THE INVENTION

This invention relates generally to magnetic resonance imaging (MRI). Magnetic resonance imaging (MRI) is a non-destructive method for the analysis of materials and is an approach to medical imaging. It is generally non-invasive and does not involve ionizing radiation. In very general terms, nuclear magnetic moments are excited at specific spin precession frequencies which are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

Magnetic resonance (MR) imaging is based on nuclear spins, which can be viewed as vectors in a three-dimensional space. During an MRI experiment, each nuclear spin responds to four different effects: precession about the main magnetic field, nutation about an axis perpendicular to the main field, and both transverse and longitudinal relaxation. In steady-state MRI experiments, a combination of these effects occurs periodically.

SUMMARY OF THE INVENTION

In accordance with the invention, a method for musculoskeletal tissue segmentation in magnetic resonance imaging (MRI) is provided. MRI image data is collected using at least two different contrast mechanisms. Voxel values from data from each contrast mechanism are used as elements of a feature vector. The feature vector is compared with classification boundaries to classify musculoskeletal tissue type of the voxel. The previous two steps are repeated for a plurality of voxels. An image is generated from the classified musculoskeletal tissue types for the plurality of voxels to provide a musculoskeletal segmentation image.

In another manifestation of the invention, a method for generating classification boundaries for magnetic resonance imaging (MRI) for musculoskeletal tissue segmentation is provided. MRI image data is collected using at least two different contrast mechanisms. Voxel values from data from each contrast mechanism are used as elements of a feature vector. Each feature vector is marked to a musculoskeletal tissue type. The previous two steps are repeated for a plurality of voxels. At least one hyperplane is generated separating clusters of feature vectors of different musculoskeletal tissue types for the plurality of voxels.

The invention and objects and features thereof will be more readily apparent from the following detailed description and appended claims when taken with the drawings.

DETAILED DESCRIPTION OF ILLUSTRATED EMBODIMENTS

Figure 1:
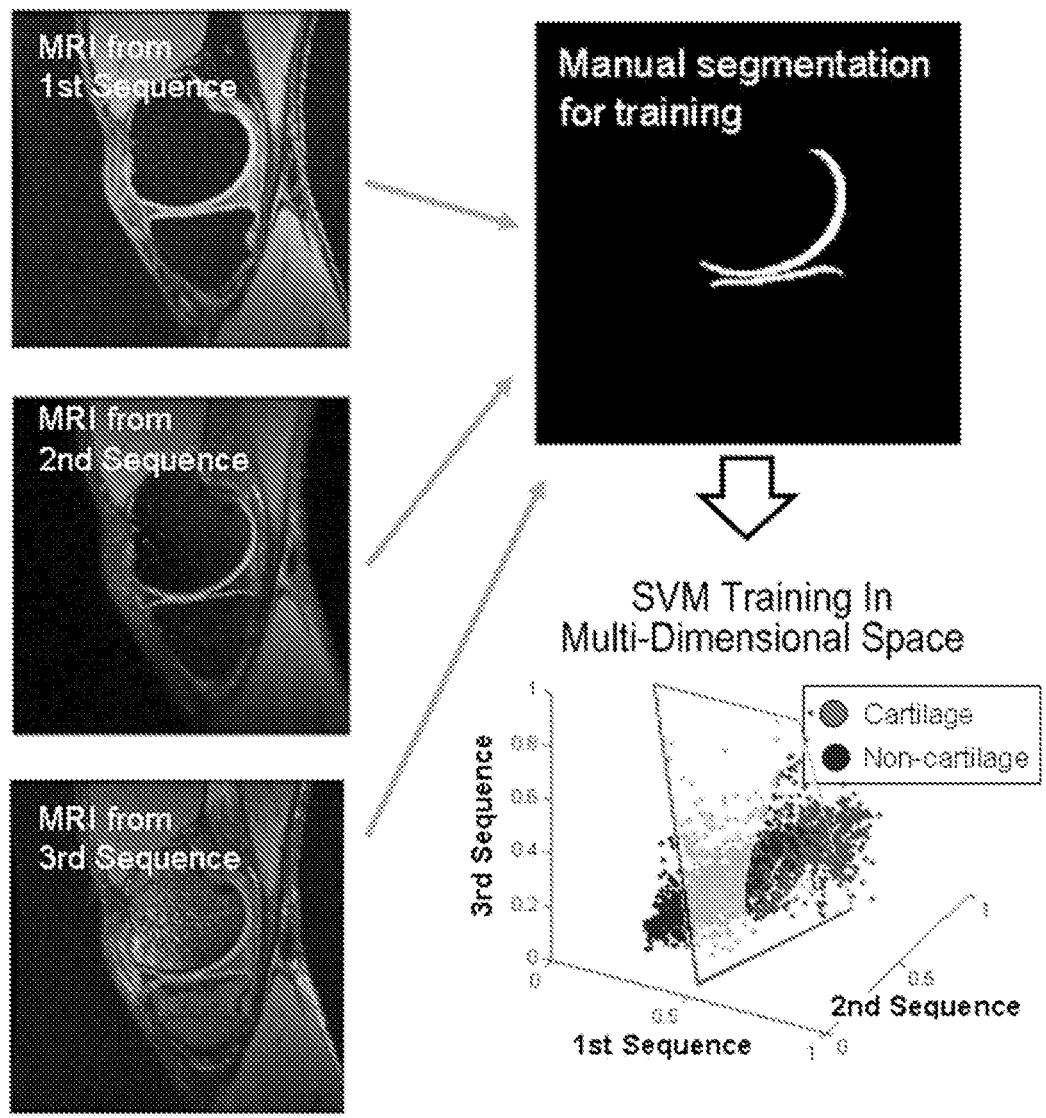
FIG. 1 shows a process that uses MR image data from three different contrast mechanisms, which are used along with the manual segmentation of articular cartilage to calculate an optimal hyperplane, which is also called training.

An analysis of articular cartilage regional morphology (thickness or volume) is frequently used for evaluating the initiation and progression of osteoarthritis. MRI can provide a non-invasive method to assess the morphology of articular cartilage. Quantifying regional cartilage thickness or volume requires MR image segmentation (classification) and three-dimensional reconstruction. The osteoarthritis initiative project that is funded by NIH and is being conducted at four clinical centers has tested 4,796 subjects with and without knee osteoarthritis in United States and obtained knee MR images for 2686 participants with five different MR sequences between 2004 and 2006. The subjects will be followed every year for up to four years. Though an enormous number of MR images have been obtained, there is a lack of tools to process the data. The MR images are being released to research institutions by request for processing and analyzing the data, typically requiring 1-2 hours per knee by highly-trained specialists for cartilage segmentation. In addition, three-dimensional models of cartilage can help better quantify and visualize the disease on articular cartilage in clinics. Thus, more automated or fully-automated segmentation is being sought.

Vannier et. al. in "Technical Developments and Instrumentation: Multispectral Analysis of Magnetic Resonance Images," Radiology, Vol. 154, No. 1, pp 221-224, January 1985, which is incorporated by reference for all purposes, discusses the use of multispectral analysis of magnetic resonance imaging.

Previously, numerous computational methods have been used in the attempt to segment articular cartilage from a single set of gray scale MR images taken with a single sequence. Yet, fully automatic segmentation seems to be a difficult goal to achieve. There exist many different MR sequences that utilize tissue properties such as T1 and T2 relaxation times to increase the contrast between cartilage and its surrounding soft tissues in joints. Though the methods of using multiple sets of MR images or images from multiple modalities such as PET and SPECT that provide different contrasts have been suggested for brain and cancer imaging, such as Bezdek J C, Hall L O, Clarke L P, "Review of MR image segmentation techniques using pattern recognition," Med Phys. 20(4): 1033-1048, 1993 and Clarke L P, Velthuizen R P, Camacho M A, Heine J J, Vaidyanathan M, Hall L O, Thatcher R W, Silbiger M L, "MRI segmentation: Methods and applications," Magnetic Resonance Imaging 3(3):343-368, 1995, which are incorporated by reference for all purposes, these have not been actually applied for cartilage segmentation. Multiple sets of MR images taken with different sequences provide different contrast mechanisms between tissues and will help separate different tissues. Over the last decade, numerous alternative sequences that significantly improve the cartilage signal to noise ratio, and also which provide different image contrast have been investigated.

An embodiment of the invention uses a novel algorithm to segment articular cartilage automatically from MR images utilizing multiple sets of MR images specific for articular cartilage using a support vector machine (SVM) method described in Vapnik V N. *Nature of Statistical Learning Theory*, Springer, 1995, and in Hastie T, Tibshirani R, Friedman J H, *The Elements of Statistical Learning*, Springer, 2003, which is incorporated by reference for all purposes.

DESCRIPTION

Data Acquisition:

Multiple sets of MR images are taken for a joint of interest in the body with different MR sequences. Each MR sequence provides a unique mechanism to produce contrast between articular cartilage and different non-cartilage tissues. Spatial alignment between the multiple sets of MR images should be confirmed. Each pixel (or voxel) in the image (or volume) thus has multiple gray scale values from the multiple sets of MR images and a feature vector consists of the gray scale values can be formed for each pixel (voxel).

Training of SVM:

The training is required ideally only once with a sample joint, and then can be applied to process new data from similar joints of different people. The data for training consists of multiple sets of MR images for a joint of interest from a subject and binary mask images of articular cartilage which is manually segmented from one of the multiple sets of MR images. As stated previously a feature vector can be formed for each pixel (voxel), thus, conceptually speaking, each pixel (voxel) is mapped to a point in a multi-dimensional space (with dimension equal to the number of sets of MR images) and marked as either black or white according to the binary value of the pixel (voxel) in the mask images. For example, the pixels (voxels) of cartilage and non-cartilage tissues are white and black, respectively. The SVM calculates an optimal hyperplane that separates the pixels (voxels) of cartilage from the pixels (voxels) of non-cartilage tissues as shown in FIG. 1. For the calculation, a canned machine learning software package can be used. Examples of canned machine learning software packages are the Spider machine learning package for MATLAB, which is available at kyb.tuebingen.mpg.de/bs/people/spider/ and SVM light, which is available at svm-light.joachims.org/.

FIG. 1 shows a process that uses MR image data from three different contrast mechanisms, which are used along with the manual segmentation of articular cartilage to calculate an optimal hyperplane that separates cartilage and non-cartilage pixels in a multi-dimensional intensity space.

Segmentation with Trained SVM:

Once the SVM is trained and an optimal separation hyperplane is calculated, the SVM can be used to segment cartilage from new data sets. This step is also called a classification. A new data set consists of multiple sets of MR images with the same MR sequences used in the training. A feature vector is formed for each pixel (voxel) with the gray scale values from the multiple sets of MR images. Each pixel (voxel) is tested by the trained SVM to be determined whether the pixel (voxel) is inside or outside of the hyperplane representing the boundary of cartilage pixels (voxels) as shown in FIG. 2.

Figure 2:
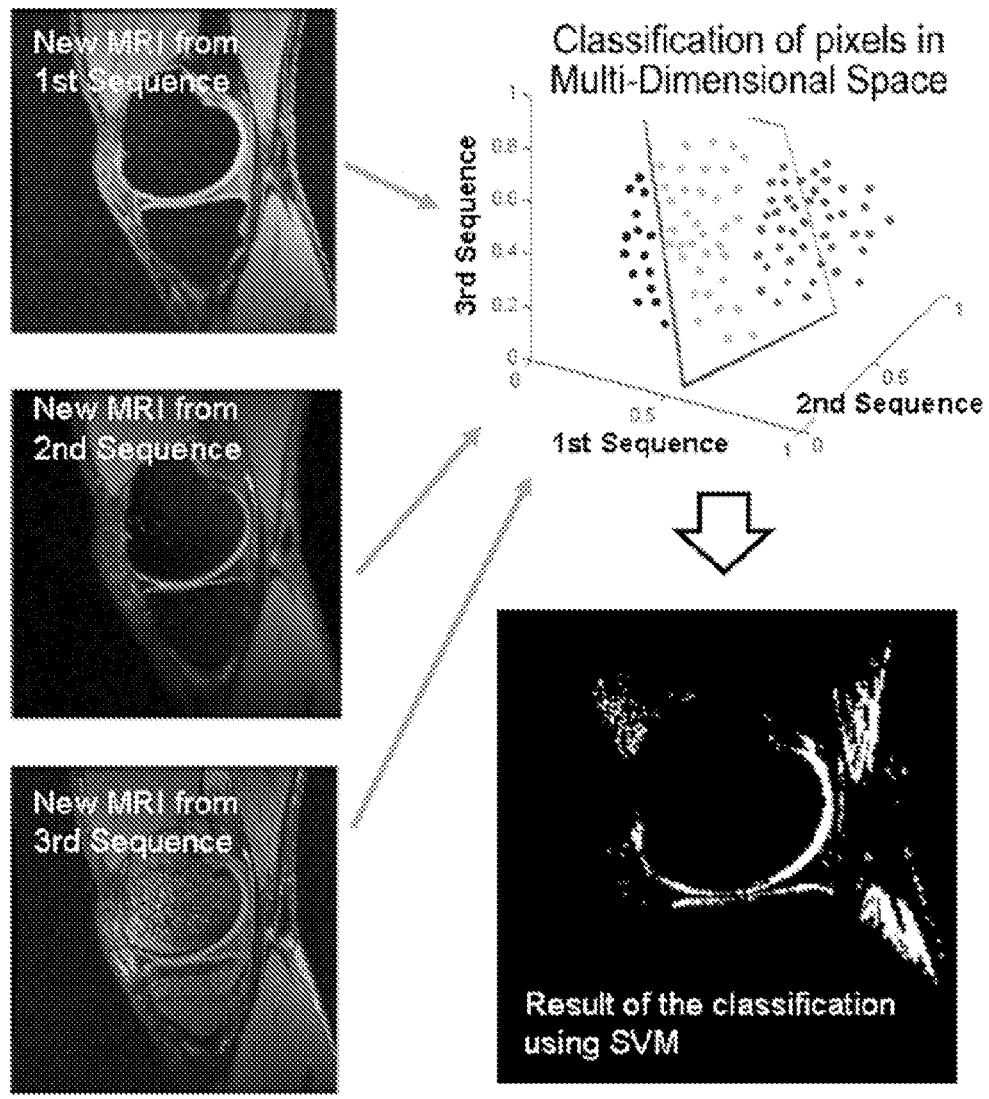
FIG. 2 shows a process that uses MR image data from the same three different contrast mechanisms used in training, that can classify pixels in the MR image data for automatic segmentation of cartilage using the optimal hyperplane calculated during training.

FIG. 2 shows a process that uses MR image data from the same three different contrast mechanisms used in training, can classify pixels in the MR image data for automatic segmentation of cartilage using the calculated optimal hyperplane that separates cartilage and non-cartilage pixels in a multi-dimensional intensity space.

Once the segmentation is complete for a data set, then a three-dimensional model can be created with additional post processing steps.

Generalized Process

Figure 3:
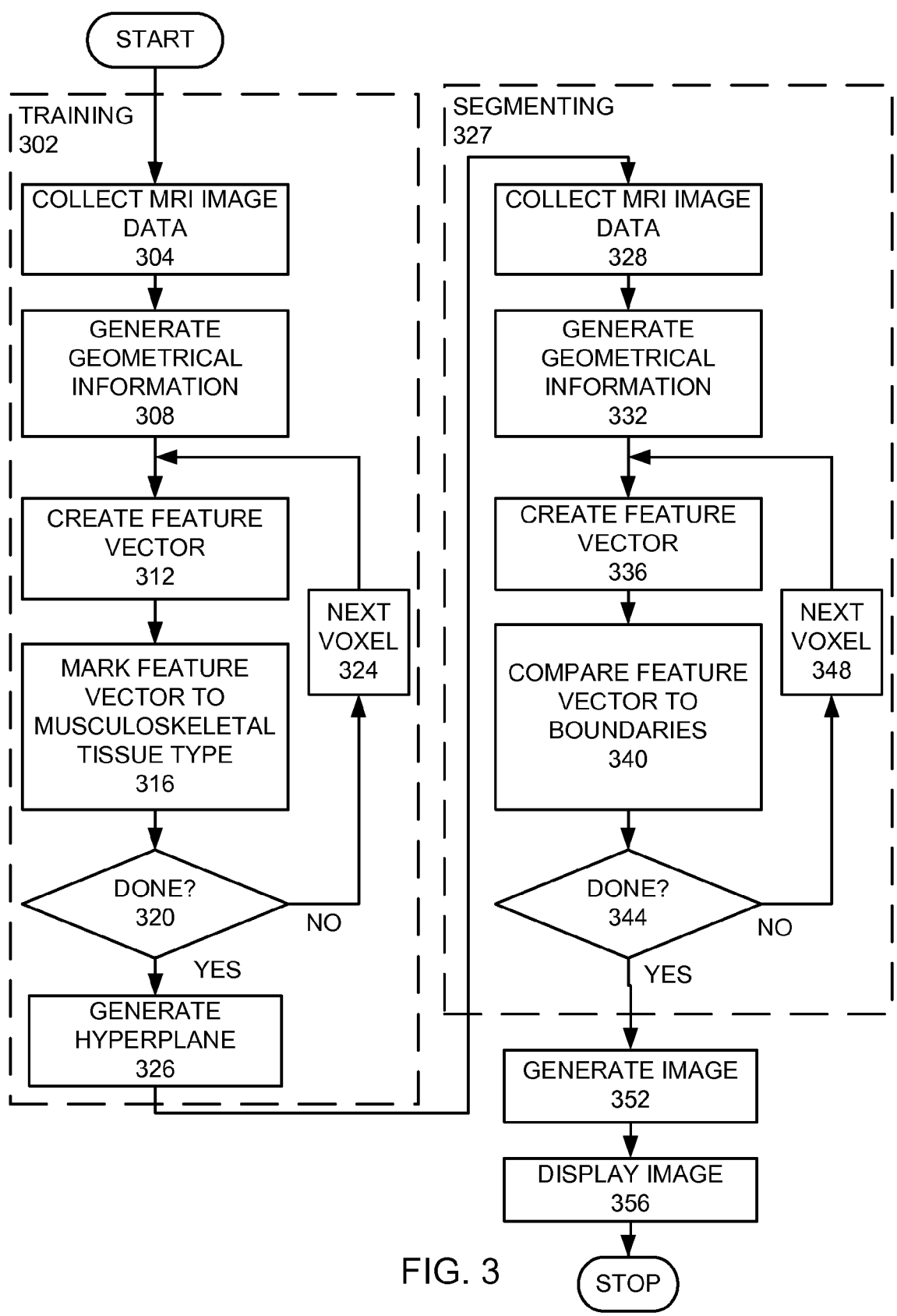
FIG. 3 is a high level flow chart of an embodiment of the invention.

To facilitate understanding, FIG. 3 is a high level flow chart of an embodiment of the invention. A training process is first and once performed to generate classification boundaries for musculoskeletal tissue segmentation (step 302). MRI data is collected using at least two different contrast mechanisms (step 304). The MRI data is used to generate geometrical information for voxels in the MRI data (step 308). Such geometrical information may be distance from the bone. The use of the geometrical information of distance from the bone helps to distinguish muscle from cartilage, since articular cartilage is always adjacent to the end of the bone, and muscle further away. To obtain the geometrical information, the MRI image data may be used to first obtain anatomical information, which is then used to obtain the geometrical information. This is helpful, since in many proton MRI sequences it is difficult to distinguish cartilage from muscle using only gray scale values. A feature vector is created for a voxel (step 312). The MRI data for a voxel for each contrast mechanism is used as a vector dimension and the generated geometrical information for the voxel is also used as vector dimension to generate the feature vector. If geometrical information is not generated, then geometrical information is not used in the feature vector. The feature vector is marked to musculoskeletal tissue type (step 316). A determination is made on whether all voxels have been marked (step 320). If not, a next voxel is selected (step 324) and then steps 312 and 316 are performed, until all voxels are completed. At least one hyperplane is generated (step 326), where the hyperplane separates clusters of feature vectors of different musculoskeletal tissue types for the plurality of voxels. The training is completed.

Using the hyperplanes generated from the training process, an MRI musculoskeletal segmentation process may be achieved (step 327). MRI image data is collected using the same contrast mechanisms as in the training process, but on a similar joint of a different person (step 328). The MRI data is used to generate geometrical information (step 332). Such geometrical information is the same type of geometrical information generated during the training. A feature vector is created for a voxel (step 336). The MRI data for a voxel for each contrast mechanism is used as a vector dimension and the generated geometrical information for the voxel is also used as vector dimension to generate the feature vector. If geometrical information is not generated, then the geometrical information is not used in the feature vector. The feature vector is compared to classification boundaries defined by the at least one hyperplane to determine musculoskeletal tissue type (step 340). A determination is made on whether all voxels have been classified (step 344). If not, a next voxel is selected (step 348) and then steps 336 and 340 are performed, until all voxels are completed. The classified voxels are then used to generate an image and a three-dimensional model (step 352). The image and model are displayed (step 356).

Figure 4:
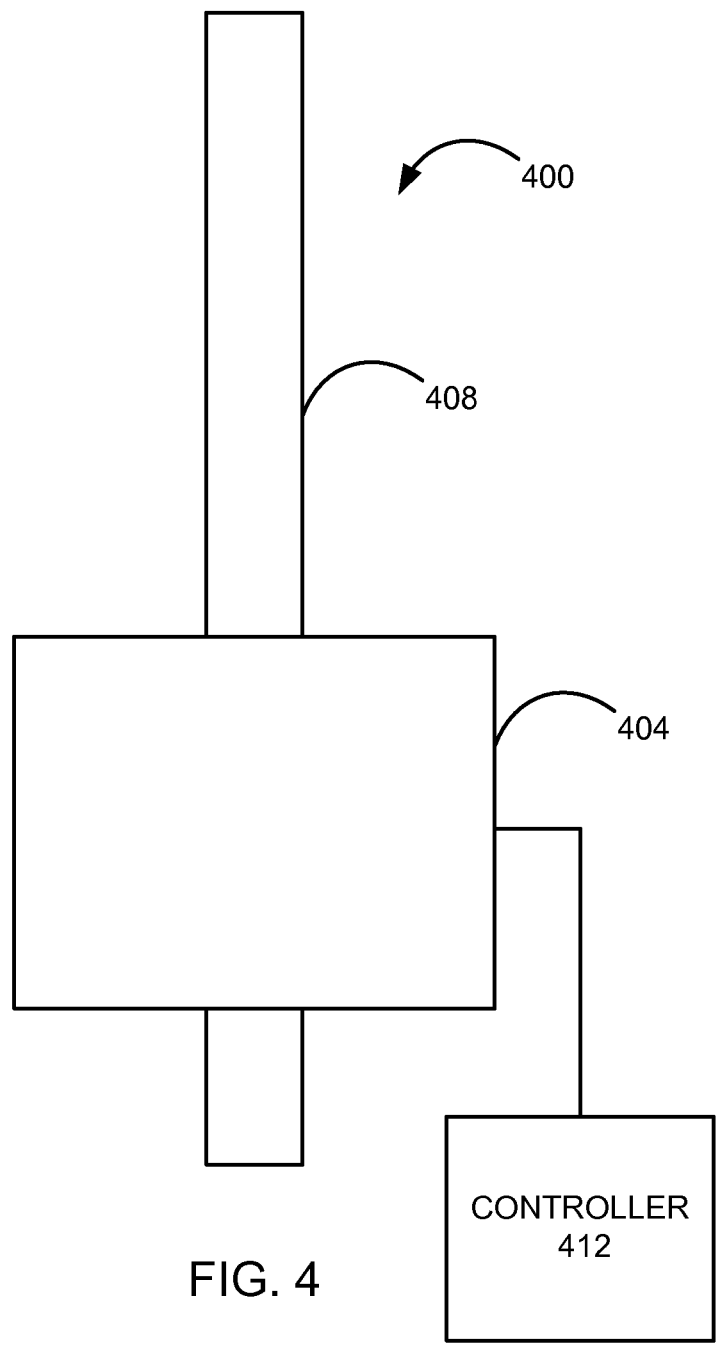
FIG. 4 is a schematic top view of a magnetic resonance imaging (MRI) system that may be used in an embodiment of the invention.

FIG. 4 is a schematic top view of a magnetic resonance imaging (MRI) system 400 that may be used in an embodiment of the invention. The MRI system 400 comprises a magnet system 404, a patient transport table 408 connected to the magnet system, and a controller 412 controllably connected to the magnet system. In one example, a patient would lie on the patient transport table 408 and the magnet system 404 would pass around the patient. The controller 412 would control magnetic fields and radio frequency (RF) signals provided by the magnet system 404 and would receive signals from detectors in the magnet system 404. In one embodiment, the magnet system 404 would use a single excitation coil to excite the first volume and the second volume. In another embodiment, the magnet system 404 would use multiple excitation coils to excite the first volume and the second volume. For imaging a small volume, such as around the knee or other joint, a movably patient transport table may not be needed, but instead the magnet system 404 may be placed around the knee or other joint.

Figure 5A:
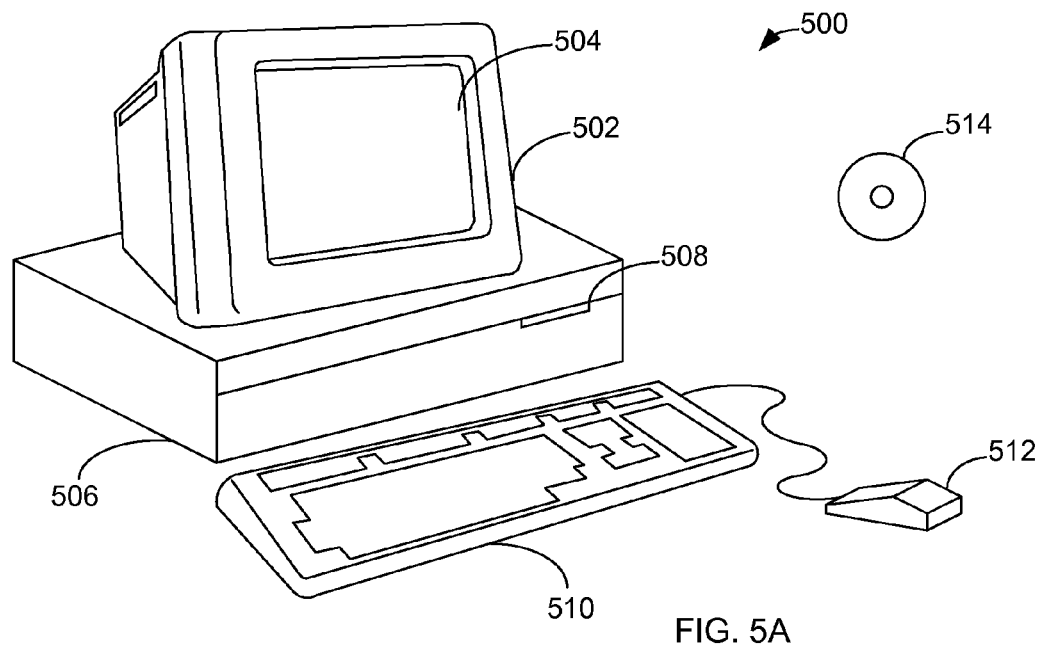
FIGS. 5A and 5B illustrate a computer system that may be used in an embodiment of the invention.
Figure 5B:
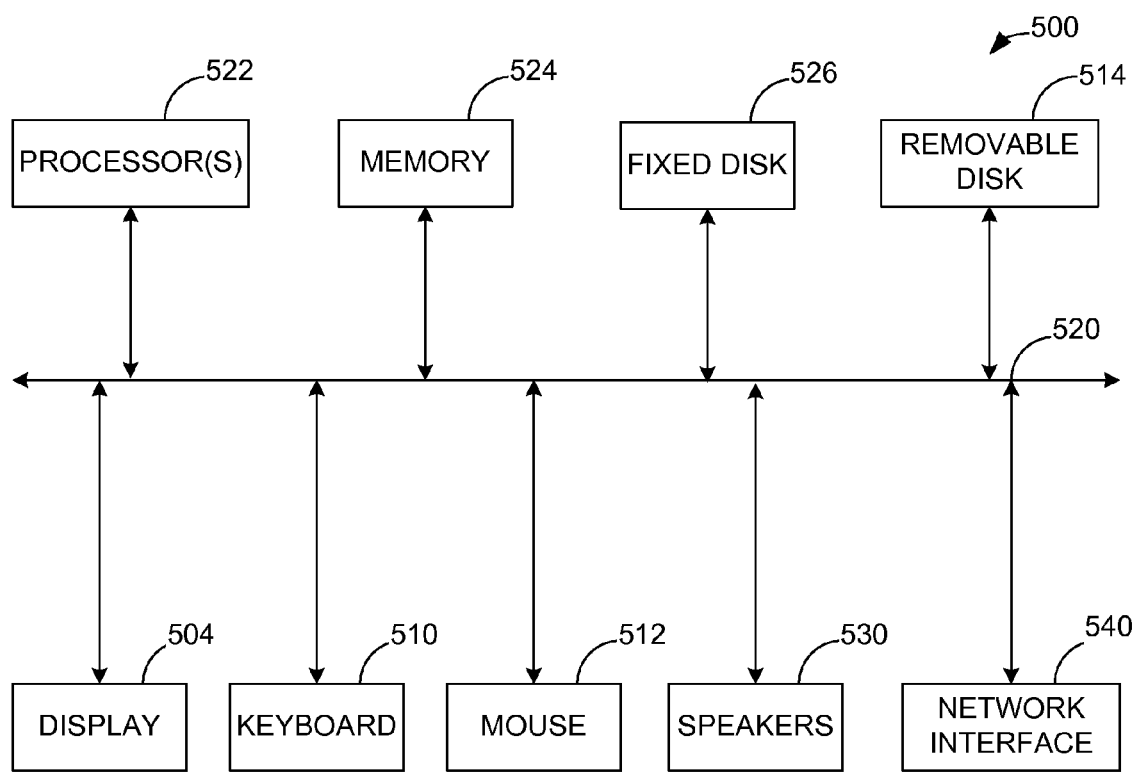

FIGS. 5A and 5B illustrate a computer system 500, which is suitable for implementing a controller 412 used in embodiments of the present invention. FIG. 5A shows one possible physical form of the computer system. Of course, the computer system may have many physical forms ranging from an integrated circuit, a printed circuit board, and a small handheld device up to a huge super computer. Computer system 500 includes a monitor 502, a display 504, a housing 506, a disk drive 508, a keyboard 510, and a mouse 512. Disk 514 is a computer-readable medium used to transfer data to and from computer system 500.

FIG. 5B is an example of a block diagram for the computer system 500. Attached to system bus 520 are a wide variety of subsystems. Processor(s) 522 (also referred to as central processing units, or CPUs) are coupled to storage devices, including memory 524. Memory 524 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 526 is also coupled bi-directionally to CPU 522; it provides additional data storage capacity and may also include any of the computer-readable media described below. Fixed disk 526 may be used to store programs, data, and the like and is typically a secondary storage medium (such as a hard disk) that is slower than primary storage. It will be appreciated that the information retained within fixed disk 526 may, in appropriate cases, be incorporated in standard fashion as virtual memory in memory 524. Removable disk 514 may take the form of the computer-readable media described below.

CPU 522 is also coupled to a variety of input/output devices, such as display 504, keyboard 510, mouse 512, and speakers 530. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 522 optionally may be coupled to another computer or telecommunications network using network interface 540. With such a network interface, it is contemplated that the CPU might receive information from the network, or might output information to the network in the course of performing the above-described method steps. Furthermore, method embodiments of the present invention may execute solely upon CPU 522 or may execute over a network such as the Internet in conjunction with a remote CPU that shares a portion of the processing.

In addition, embodiments of the present invention further relate to computer storage products with a computer-readable medium that has computer code thereon for performing various computer-implemented operations. The media and computer code may be those specially designed and constructed for the purposes of the present invention, or they may be of the kind well known and available to those having skill in the computer software arts. Examples of tangible computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Experiment 1

Using a Cadaveric Knee

Data Acquisition:

Four three-dimensional (3D) MR sequences, spoiled gradient recalled echo (SPGR), double echo steady state (DESS), balanced steady state free precession (FIESTA) and IDEAL gradient echo (GRE) were run on an intact cadaveric knee to get six sets of MR images (two sets from each SPGR and FIESTA, two sets (first and second echo images) from DESS, and two sets (water and fat images) from IDEAL-GRE) within 30 minutes. The registrations between the MR images from different sequences were confirmed.

Geometric Information:

Bones in the MR images were automatically segmented using a simple threshold-based method on SPGR and IDEAL-GRE images. The centers in both of the distal femoral condyles were automatically detected. Using this automatic bone segmentation and femoral bone feature detection, distance from the closest bone, relative location along the medial and lateral center of the distal femur, and angle between the main magnetic direction of the MRI and the line to the femoral center line were calculated as geometric information for each pixel.

Training of SVM:

The pixels that consist of the articular cartilage were manually identified using the SPGR MR images in every fifth slices. Both the cartilage and non-cartilage pixels were input to a SVM. The SVM, conceptually speaking, mapped each pixel to a nine-dimensional vector space (six dimensions from the six sets of MRI data and three dimensions from the three different sets of geometric information) and calculated an optimal hyperplane that separates the cartilage pixels from non-cartilage pixels as shown in FIG. 1. For the calculation of the hyperplane, the SVM-light was used as described in Joachims T, SVM light, http://svmlightjoachims.org/.

Segmentation with Trained SVM:

As with the pixels used for the training, the rest of pixels in the MRI data also had nine components in the same order. Each pixel was tested by the trained SVM to determine whether the pixel was inside or outside of the hyperplane representing the boundary of cartilage pixels in the nine-dimensional space. To assess the performance of the SVM, the cartilage in all slices were manually segmented as a gold standard, and the sensitivity and specificity of the classification results and the geometrical deviation were calculated.

Results

Figure 6:
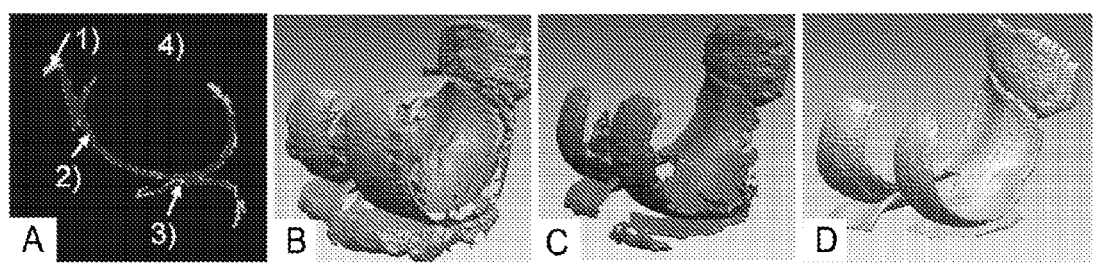
FIGS. 6A-D illustrate the results of an experiment with a cadaveric knee.

True positive, false positive, true negative and false negative pixels were counted from the classification result, as shown in FIG. 6A. The sensitivity and specificity were 98.95% and 97.91%, respectively, and the geometric deviation on cartilage surface was 0.4±0.5 mm in average (SD). When only the pixels more inside of the SVM cartilage boundary were selected, the geometric deviation on cartilage surface decreased significantly (0.0±0.6 mm). Three-dimensional models were created from the classification result and the manual segmentation for qualitative comparison as shown in FIGS. 6B-D.

FIGS. 6A-D illustrate the results. FIG. 6A shows the classification result of a slice, where a false positives are shown at 1, a true positive is shown at 2, a false negative is shown at 3, and a true negative is shown at 4. FIGS. 6B and 6C are 3D models of the classification results when all pixels inside the hyperplane were used and when the pixels more inside (higher probability to be cartilage pixel) of the hyperplane were used, respectively. FIG. 6D is a 3D model from the manual segmentation (gold standard).

The results show that for all true cartilage pixels, 98.95% of pixels were classified as cartilage pixels. The sensitivity in this study was higher than the sensitivity reported in a recent study using another method, as described in Folkesson J. et al, IEEE Trans Med Imaging, 26(1):106-15, 2007, which is incorporated by reference for all purposes. This shows the possibility of using the signal intensities from multiple MR images along with geometric information as features for SVM to automatically segment articular cartilage. Ideally, the training is required only once to determine the hyperplane of SVM and then, the hyperplane can be used to automatically segment articular cartilage from new data sets from the joints from other subjects.

Experiment 2

Using Two Knees from Two Healthy Volunteers

Data Acquisition:

Three three-dimensional (3D) MR sequences, spoiled gradient recalled echo (SPGR), balanced steady state free precession (FIESTA) and IDEAL gradient echo (GRE) were run on the knees of two healthy volunteers to get four sets of MR images (two sets from each SPGR and FIESTA, and two sets (water and fat images) from IDEAL-GRE) within 30 minutes. The registrations between the MR images from different sequences were confirmed.

Geometric Information:

In addition to the geometric information used in experiment 1, gradient matrix calculated using the bone distance matrix was added in this experiment.

Training of SVM:

The MRI data and the geometric information obtained from the cadaveric knee in experiment 1 was used for training of SVM. In this in vivo study, we used only three MR sequences which is the subset of sequences used in the cadaveric knee experiment and added new geometric information (gradient matrix), thus the data from the cadaveric knee were reorganized to calculate an optimal hyperplane in eight dimensional space (four dimensions from the four sets of MRI data and four dimensions from the four different geometric information).

Segmentation with Trained SVM:

As in the experiment 1, a feature vector with eight components in the same order as in training were formed for each pixel and tested by the trained SVM to determine whether the pixel was inside or outside of the hyperplane representing the boundary of cartilage pixels in the eight-dimensional space. To assess the performance of the SVM, the cartilage in all slices were manually segmented as a gold standard, and the sensitivity and specificity of the classification results were calculated.

Result

The sensitivity and specificity of the classification results were 96.5% and 98.2%, respectively, for the first knee and 88.4% and 98.8%, respectively, for the second knee. Three-dimensional models were created from the classification result and the manual segmentation for qualitative comparison as shown in FIGS. 7A-D.

Figure 7:
FIGS. 7A-D illustrate the results of an experiment with two knees from two healthy volunteers.

FIGS. 7A-D illustrate the results. FIGS. 7A and 7C show the cartilage models from the automatic segmentation of MRI data of the first and second subjects, respectively. FIGS. 7B and 7D show the cartilage models from the manual segmentation of the MRI data of the first and second subjects, respectively, as gold standards.

This embodiment of the invention provides automatic segmentation (classification) of cartilage and non-cartilage pixels. Embodiments of the invention can also be applied to other musculoskeletal tissues of interests in the joint, such as bone, cartilage, muscle, meniscus, and ligament as long as there are sufficient MR sequences to provide unique contrast mechanisms for the target tissues.

This embodiment of the invention is based on a machine learning method, thus the training process determines the results of segmentation. The training data set can be optimized to provide a maximum separation between cartilage and non-cartilage pixels (voxels) by fine tuning the parameters of MR sequences and utilizing different properties of tissues such as T1, T2, sodium and magnetization transfer. An increased number of training data sets would usually improve the performance of segmentation.

Most of the current methods for articular cartilage segmentation are based on somewhat edge detection techniques using a single set of MR images, which may suffer from blurry or ambiguous tissue boundaries in a set of MR images. The chance of detecting the correct boundaries increases by utilizing multiple sets of MR images with different contrasts.

For various embodiments of the invention different contrasts for cartilage can be obtained using the MR sequences available in commercial MR machines. The software to process MR images to prepare input data for SVM exists as a Matlab prototype that can easily be added to commercial reconstructions.

For various embodiments of the invention, linear and non-linear kernels can be used for SVM. Machine learning algorithms other than SVM can be used such as artificial neural networks and K-nearest neighbor.

In various embodiments, the classification process can be not only binary, but also multiple classifications to segmentation multiple tissues such as cartilage, muscle, bone and meniscus at the same time.

Various embodiments use anatomical information of the joint such as the shape of articular cartilage and some type of connected-region constraint or shape of the bone to provide geometrical information to remove spurious (scattered) pixels (voxels) and increase the accuracy. In another embodiment, the geometrical information may be angle information, such as the angle between a line that connect the voxel and a feature in the bone and the direction of the main magnetic field. In another embodiment, the geometrical information is the relative location along two features on the bone. In one embodiment, at least three different contrast mechanisms are used, where one of the contrast mechanisms is SPGR. In such an embodiment, one of the at least three contrast mechanisms may also be at least one of balanced SSFP, DESS, IDEAL gradient-echo, 3D fast spin-echo, and Magnetization Transfer.

In other embodiments, other contrast mechanisms that may be used in embodiments of the invention are fluid-attenuated inversion recovery (FLAIR), turbo spin echo (TSE), T1 map and T2 map.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention

What is claimed is:

1. A method for magnetic resonance imaging (MRI) for musculoskeletal tissue segmentation, comprising:
   a) collecting MRI image data using at least two different-three-dimensional (3D) MR sequences;
   b) using voxel values from data from each 3D MR sequence as elements of a feature vector;
   c) comparing the feature vector with classification boundaries to classify musculoskeletal tissue type of the voxel;
   d) repeating steps b-c for a plurality of voxels;
   e) generating an image from the classified musculoskeletal tissue types for the plurality of voxels to provide a musculoskeletal segmentation image;
   f) processing the collected MRI image data to obtain anatomical information;
   g) generating additional geometrical information for each voxel from the anatomical information; and
   h) using the generated additional geometrical information as elements of the feature vector along with the voxel values from the collected MRI image data.

2. The method, as recited in claim 1, wherein at least three different 3D MR sequences are used.

3. The method, as recited in claim 2, wherein one of the at least three different D MR sequences is SPGR (spoiled gradient recalled echo).

4. The method, as recited in claim 3, wherein at least one of the three different 3D MR sequences is at least one of balanced SSFP (steady state free precession), double-echo steady state, IDEAL (iterative decomposition of water and fat with echo asymmetry and least-squares estimation) gradient-echo, 3D (three dimensional) fast spin-echo, and Magnetization Transfer.

5. The method, as recited in claim 4, wherein the musculoskeletal tissue types are bone, cartilage, muscle, meniscus, and ligament.

6. The method, as recited in claim 4, wherein the musculoskeletal tissue types are cartilage and non-cartilage.

7. The method, as recited in claim 4, further comprising generating the classification boundaries, comprising:
   i) collecting second MRI image data using at least two different 3D MR sequences;
   j) using voxel values from data from each 3D MR sequence as elements of a second feature vector;
   k) assigning the second feature vector to a musculoskeletal tissue type;
   l) repeating steps f-h for a plurality of voxels; and
   m) generating at least one hyperplane separating clusters of feature vectors of different musculoskeletal tissue types for the plurality of voxels.

8. The method, as recited in claim 7, wherein the assigning each feature vector uses a manual classification.

9. The method, as recited in claim 8, wherein the generating the hyperplane uses machine learning.

10. The method, as recited in claim 1, wherein the anatomical information comprises location and shape of bone and the additional geometrical information comprises distance from the closest bone surface, angle between tissue surface normal direction and the direction of the main magnetic field.

11. A method for generating classification boundaries for magnetic resonance imaging (MRI) for musculoskeletal tissue segmentation, comprising:
   a) collecting MRI image data using at least two different three-dimensional (3D) MR sequences;
   b) using voxel values from data from each 3D MR sequence as elements of a feature vector;
   c) marking each feature vector to a musculoskeletal tissue type;
   d) repeating steps b-c for a plurality of voxels;
   e) generating at least one hyperplane separating clusters of feature vectors of different musculoskeletal tissue types for the plurality of voxels;
   f) processing the collected MRI image data to obtain anatomical information;
   g) generating additional geometrical information for each voxel from the anatomical information; and
   h) using the generated additional geometrical information as elements of the feature vector along with the voxel values from the collected MRI image data.

12. The method, as recited in claim 11, wherein the marking each feature vector uses a manual classification.

13. The method, as recited in claim 12, wherein the generating the hyperplane uses machine learning.

14. The method, as recited in claim 13, wherein one of the at least two different-3D MR sequences is SPGR.

15. The method, as recited in claim 14, wherein at least one of the at least two different 3D MR sequences is selected from the group of balanced SSFP, double-echo steady state, IDEAL gradient-echo, 3D fast spin-echo, and Magnetization Transfer.

16. The method, as recited in claim 15, wherein the musculoskeletal tissue types are at least two of bone, cartilage, muscle, meniscus, and ligament.

17. The method, as recited in claim 15, wherein the musculoskeletal tissue types are cartilage and non-cartilage.

* * * * *